United States Patent [19]

Dorn et al.

[11] 4,046,897

[45] Sept. 6, 1977

[54] 5-MERCAPTOPYRIDOXINE ALKANESULFONATES AND METHODS OF USE AND PHARMACEUTICAL COMPOSITIONS

[75] Inventors: Conrad P. Dorn, Plainfield; Howard Jones, Holmdel; David P. Jacobus, Princeton, all of N.J.

[73] Assignee: Merck & Co., Inc., Rahway, N.J.

[21] Appl. No.: 666,536

[22] Filed: Mar. 15, 1976

Related U.S. Application Data

[63] Continuation-in-part of Ser. No. 576,055, May 9, 1975, abandoned.

[51] Int. Cl.$^2$ .................. A61K 31/44; C07D 213/62
[52] U.S. Cl. ........................... 424/263; 260/294.8 G
[58] Field of Search ................ 424/203; 260/294.8 G

[56] References Cited

U.S. PATENT DOCUMENTS

| | | | |
|---|---|---|---|
| 3,010,966 | 11/1961 | Zinia et al. | 260/294.8 |
| 3,755,336 | 8/1973 | Schorre et al. | 260/294.8 G |
| 3,852,454 | 12/1974 | Jaffe | 424/263 |

*Primary Examiner*—Stanley J. Friedman
*Attorney, Agent, or Firm*—Frank M. Mahon; Raymond M. Speer

[57] ABSTRACT

5-Mercaptopyridoxine $C_{1-4}$ alkane sulfonates, particularly the ethane-1,2-disulfonate, is a superior pharmaceutically acceptable form of the previously preferred 5-mercaptopyridoxine hydrochloride and hydrobromide.

6 Claims, No Drawings

5-MERCAPTOPYRIDOXINE ALKANESULFONATES AND METHODS OF USE AND PHARMACEUTICAL COMPOSITIONS

This application is a continuation-in-part of prior co-pending application Ser. No. 576,055, filed May 9, 1975 now abandoned.

This invention is concerned with pharmaceutically acceptable alkanesulfonic acid addition salts of 2-methyl-3-hydroxy-4-hydroxymethyl-5-mercaptomethylpyridine, a physically, chemically, and pharmaceutically improved form of the known pharmacologically active 2-methyl-3-hydroxy-4-hydroxymethyl-5-mercaptomethylpyridine (5-mercaptopyridoxine or 5-MP).

In particular, this invention is concerned with $C_{1-4}$ alkanesulfonic and $C_{1-4}$ alkanedisulfonic acid addition salts of 5-mercaptopyridoxine of formula:

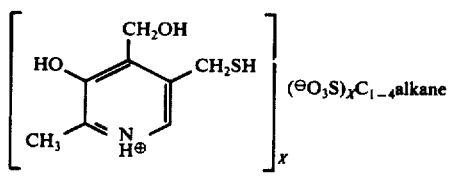

$$\left[ \begin{array}{c} \text{HO} \overset{\text{CH}_2\text{OH}}{\diagup} \text{CH}_2\text{SH} \\ \text{CH}_3 \diagdown \underset{\overset{\text{N}}{\text{H}\oplus}}{} \diagup \end{array} \right]_x (\ominus O_3S)_x C_{1-4}\text{alkane}$$

where X is 1 or 2, and $C_{1-4}$ alkane is either straight or branched chain; a process for their preparation, a method of treating rheumatoid arthritis and pharmaceutical compositions comprising a novel compound. Even more particularly, it is concerned with the ethane-1,2-disulfonic acid addition salt (edisylate) of 5-mercaptopyridoxine, a process for its preparation, a method of treating rheumatoid arthritis with it, and pharmaceutical compositions.

The compound, 5-mercaptopyridoxine, has been reported to be pharmacologically active as a radiation protective agent and an anti-rheumatoid arthritic agent, preferably in the form of a salt with a pharmaceutically acceptable acid. The preferred salt is stated to be the hydrochloride or hydrobromide.

It has been found that most, if not all, of the salts specifically reported in the prior art, and certainly the hydrochloride, the previously preferred salt, suffer serious physical, chemical and/or pharmaceutical disadvantages by virtue of their chemical instability and other undesirable properties. Surprisingly, it has now been found that the $C_{1-4}$ alkanesulfonate and $C_{1-4}$ alkanedisulfonate salts of 5-mercaptopyridoxine, and particularly the ethane-1,2-disulfonate salt (edisylate) are substantially free of this defect and are, therefore, much superior to the previously preferred salts for formulation into pharmaceutical unit dosage forms. The superior chemical stability of the salts of this invention has been confirmed by actual comparative test.

Thus, in order to evaluate the relative stability of several salts of 5-mercaptopyridoxine, the test salts selected (i.e., the ethane-1,2-disulfonate, the phosphate, the sulfamate, the nitrate and the hydrochloride) were subjected to accelerated conditions of high temperature as the pure, unformulated, compound. The high temperature date obtained at 80° C. and at 105° C. is conventionally used in the pharmaceutical industry to screen compounds in as short a time as possible. Where a number of derivatives or salts are available, comparative data can be obtained and the test compounds can be ranked in an expected order of stability. The thermally stressed salts were assayed colorimetrically for intact thiol group. The ethanedisulfonate, hydrochloride and sulfamate salts also were subjected to NMR analysis to confirm the chemical analysis. The NMR data supports the chemical data. The accumulated data obtained is shown in Table 1 below.

TABLE 1

| Comparison of Thermal Stability of 5-MP Salts | | | | |
|---|---|---|---|---|
| | Thermal Stability % Remaining | | | |
| | 105° C | | 80° C | |
| Salt of 5-MP | 3 days | 7 days | 1 week | 3 weeks |
| Ethanedisulfonate | 97.3 | 99.4 | 101.0 | 100.2 |
| Hydrochloride | 57.3 | — | 70.5 | 57.3 |
| Sulfamate | 13.0 | 8.8 | 94.0 | 75.7 |
| Phosphate | 93.0 | 58.0 | — | — |
| Nitrate | — | — | 87.2 | — |

The data clearly shows that the ethanedisulfonate salt is the most stable salt at the temperatures employed. Based on the thermal stability advantages obviously shown by the data, the ethanedisulfate is the salt of choice.

The novel compounds of this invention are prepared by the novel process which comprises mixing 2 molar parts of 5-mercaptopyridoxine or soluble acid addition salt thereof, preferable the hydrochloride, and 2 molar parts of $C_{1-4}$ alkanesulfonic acid or 1 molar part of $C_{1-4}$ alkanedisulfonic acid or alkali metal or alkaline earth metal salt thereof, preferably the sodium salt in a liquid medium capable of dissolving to some degree the two starting materials at a temperature between ambient and reflux temperature. The product is isolated by crystallization from the liquid medium by cooling and/or concentration, if necessary. In a preferred embodiment a 5-mercaptopyridoxine hydrohalide, preferably the hydrochloride, and an alkali metal or alkaline earth metal salt of a $C_{1-4}$ alkanesulfonate or disulfonate, preferably the sodium salt, in the above-stated molar ratio, are dissolved in a minimum amount of water at ambient temperature and cooled.

Alternatively, the novel compounds of this invention may be prepared by treating bis(2,2,8-trimethyl-4-H-m-dioxino[4,5-c]pyridyl-5-methyl) disulfide with a mixture of zinc or tin dust and the desired $C_{1-4}$ alkanesulfonic acid or $C_{1-4}$ alkanedisulfonic acid in water or a suitable organic solvent. The reaction conveniently is carried out by the reaction mixture on a steam bath for about 3 to about 10 hours, preferably under an inert atmosphere. The reaction mixture is then cooled, filtered and concentrated in vacuo. The residue is extracted into refluxing organic solvent and the filtrate is filtered and cooled to precipitate the desired salt.

Similarly, the novel compounds of this invention may be prepared by treating bis(2-methyl-3-hydroxy-4-hydroxymethylpyridyl-5-methyl) disulfide with a mixture of zinc or tin dust and the desired $C_{1-4}$ alkanesulfonic acid or $C_{1-4}$ alkanedisulfonic acid in water or a suitable organic solvent. The reaction is run as described above and the desired salt is similarly recovered.

The novel compounds of this invention also may be prepared by treating 5-mercaptomethyl-2,2-8-trimethyl-4-H-m-dioxino[4,5-c]pyridine with the desired $C_{1-4}$ alkanesulfonic acid or $C_{1-4}$ alkanedisulfonic acid in water or a suitable organic solvent. In this case, the reaction mixture is usually heated on a steam bath for about 2 to about 10 hours, preferably under an inert atmosphere. The reaction is then concentrated to obtain the desired salt.

To practice the novel method of treatment of this invention, the active compounds may be administered orally, parenterally, by inhalation or rectally in dosage unit formulations containing conventional non-toxic pharmaceutically acceptable carriers, adjuvants, and vehicles. The term parenteral as used herein includes subcutaneous injections, intravenous, intramuscular, intrasternal injection or infusion techniques. In addition to the treatment of warmblooded animals such as mice, rats, horses, dogs, cats, etc., it is effective in the treatment of humans.

The pharmaceutical compositions containing the active ingredient are preferably in a form suitable for oral use, for example, as tablets, troches, lozenges, aqueous or oily suspensions, dispersible powders, or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents, coating agents and preserving agents such as antioxidants in order to provide a pharmaceutically elegant and palatable preparation.

The amount of active ingredient, alone or combined with the carrier materials, to produce a single dosage form will vary depending upon the host treated and the particular mode of administration. For example, a formulation intended for the oral administration to humans may contain from 5 mg. to 5 gm. of active agent either alone or compounded with an appropriate and convenient amount of carrier material which may vary from about 0 to about 95 percent of the total composition. Dosage unit forms will generally contain between about 50 mg. to about 1 gm. of active ingredient and preferably 500 mg.

In practicing the novel method of treatment of this invention, a formulation such as described above is administered at such a rate as to provide 1 mg. to 100 mg. per kilogram of body weight per day and preferably about 1-3 grams per human patient per day. After a latent period the benefits of treatment are realized by significant improvement in clinical and serological symptoms such as a lowering of circulating rheumatoid factor (RF) titer.

It will be understood, however, that the specific dose level for any particular patient will depend upon a variety of factors including the age, body weight, general health, sex, diet, time of administration, route of administration, rate of excretion, drug combination, previous therapy, and the severity of the particular disease undergoing therapy.

EXAMPLE 1

Bis(2-methyl-3-hydroxy-4-hydroxymethyl-5-mercaptomethyl-pyridinium) ethane-1,2-disulfonate A solution of 11.1 g. (0.05 mole) 5-mercaptopyridoxine hydrochloride in 40 ml. of water was mixed with a solution of 5.85 g. (0.025 mole) of disodium ethane-1,2-disulfonate in 40 ml. of water at room temperature. The mixture was cooled in an ice-bath until precipitation was substantially complete. The precipitate (1) was collected on a filter and the filtrate was concentrated to about 40 ml. and again cooled in an ice-bath until precipitation was substantially complete. The precipitate (2) was collected on a filter and the filtrate was concentrated to about 20 ml. and cooled in an ice-bath until precipitation was substantially complete. The precipitate (3) was collected on a filter. Precipitates (1), (2), and (3) were combined and recrystallized from methanol to give 6.5 g. of bis(2-methyl-3-hydroxy-4-hydroxymethyl-5-mercaptomethylpyridinium ethane-1,2-disulfonate, m.p. 178°-180° C.

Employing the procedure substantially as described in Example 1, but substituting for the disodium ethane-1,2-disulfonic acid used therein, an equimolar amount of the di(metal) alkanedisulfonates, or two equimolar amounts of the metal alkane sulfonates depicted in Table I, there are produced the corresponding acid addition salts of 5-mercaptopyridoxine, also depicted in Table I, in accordance with Equation I.

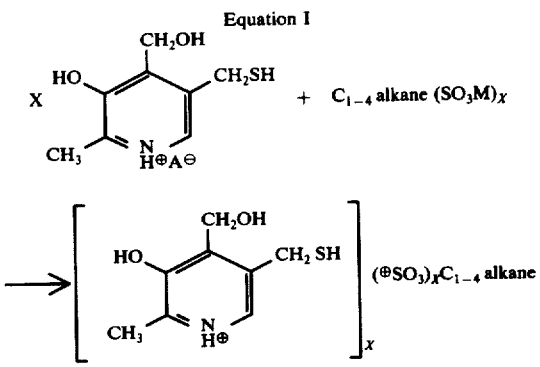

Equation I wherein
X is 1 or 2, and
A⁻ is an acid anion, and
M is an alkali metal or alkaline earth metal.

Table I

| A⊖ | M | X | $C_{1-4}$ alkane |
|---|---|---|---|
| Cl | K | 2 | $-CH_2CH_2-$ |
| Cl | Na | 2 | $-CH_2-$ |
| Cl | Na | 2 | $-(CH_2)_3-$ |
| Br | Na | 2 | $-(CH_2)_4-$ |
| Cl | K | 1 | $CH_3-$ |
| Br | K | 1 | $CH_3CH_2-$ |
| Cl | Na | 1 | $CH_3CH_2CH_2-$ |
| Br | Ca | 2 | $-CH-$<br>$\quad\;\;\|$<br>$\quad\;\;CH_3$ |
| Cl | Ca | 2 | $-CH-CH_2-$<br>$\quad\|$<br>$\quad CH_3$ |
| Br | Na | 2 | $CH_3$<br>$\;\;\|$<br>$-C-$<br>$\;\;\|$<br>$CH_3$ |

EXAMPLE 2

Bis(2-methyl-3-hydroxy-4-hydroxymethyl-5-mercaptomethyl pyridinium) ethane-1,2-disulfonate A mixture of 9.25 gm. (0.05 m) 5-mercaptopyridoxine, 4.75 gm. (0.025 m) of ethane-1,2-disulfonic acid, and 40 ml. of water is heated briefly until solution occurs. The solution is cooled and the precipitate collected by filtration. Recrystallization from methanol gives bis(2-methyl-3-hydroxy-4-hydroxymethyl-5-mercaptomethyl-pyridinium) ethane-1,2-disulfonate.

Employing the procedure substantially as described in Example 2, but substituting for the ethane-1,2-disulfonic acid used therein, an equimolar amount of the alkanedisulfonic acids or two equimolar amounts of the alkanesulfonic acids depicted in Table II, there are produced the corresponding acid addition salts also depicted in Table II, in accordance with Equation II.

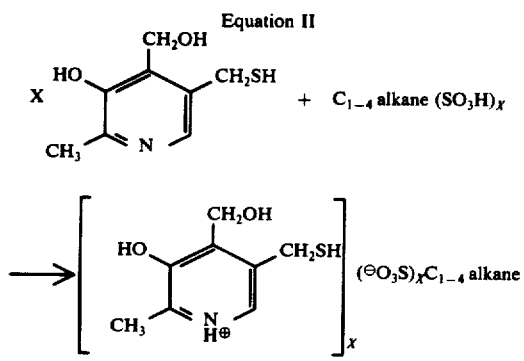

Equation II

Table II

| X | C$_{1-4}$ alkane |
|---|---|
| 2 | —CH$_2$— |
| 2 | —(CH$_2$)$_3$— |
| 2 | —(CH$_2$)$_4$— |
| 1 | CH$_3$— |
| 1 | CH$_3$CH$_2$— |
| 1 | CH$_3$CH$_2$CH$_2$— |
| 2 | —CH—<br>\|<br>CH$_3$ |
| 2 | —CH—CH$_2$<br>\|<br>CH$_3$ |
| 2 | CH$_3$<br>\|<br>—C—<br>\|<br>CH$_3$ |

EXAMPLE 3

Bis(2-methyl-3-hydroxy-4-hydroxymethyl-5-mercaptomethyl pyridinium) ethane-1,2-disulfonate Heat a mixture of 0.1 mole of bis(2,2,8-trimethyl-4H-m-dioxino[4,5-c]-pyridyl-5-methyl)disulfide, 0.2 mole of zinc dust, 0.35 mole of ethane-1,2-disulfonic acid and 200 ml. of water on a steam bath for about 5 hours under an atmosphere of nitrogen. Cool the reaction mixture, filter and concentrate in vacuo. Extract the residue with 100 ml. of boiling methanol, filter and cool the filtrate to obtain the title product.

EXAMPLE 4

Bis(2-methyl-3-hydroxy-4-hydroxymethyl-5-mercaptomethyl-pyridinium) ethane-1,2-disulfonate Heat a mixture of 0.1 mole of 5-mercaptomethyl-2,2-8-trimethyl-4H-m-dioxino[4,5-c]pyridine and 0.055 mole of ethane-1,2-disulfonic acid in 100 ml. of water on a steam bath under an atmosphere of nitrogen for about 3 hours. Concentrate the reaction to obtain the title product.

EXAMPLE 5

Bis(2-methyl-3-hydroxy-4-hydroxymethyl-5-mercaptomethyl pyridinium) ethane-1,2-disulfonate Heat a mixture of 0.1 mole of bis(2-methyl-3-hydroxy-4-hydroxymethylpyridyl-5-methyl)disulfide, 0.2 mole of zinc dust, 0.35 mole of ethane-1,2-disulfonic acid and 200 ml. of water on a steam bath for about 6 hours under a nitrogen atmosphere. Cool the reaction mixture, filter and concentrate in vacuo. Extract the residue with 100 ml. of boiling methanol, filter and cool the filtrate to obtain the title product.

Employing the procedure substantially as described in Examples 3, 4, or 5, but substituting for the ethane-1,2-disulfonic acid used therein, an equimolar amount of the alkanedisulfonic acids or two equimolar amounts of the alkanesulfonic acids depicted in Table II above, there are produced the corresponding acid addition salts as depicted in Table II in accordance with Equation II.

EXAMPLE 6

1. Tablets — 10,000 Scored tablets for oral use, each containing 500 mg. of active ingredient are prepared from the following ingredients:

|  | Gm. |
|---|---|
| bis(5-mercaptopyridoxine) ethane-1,2-disulfonate | 5000 |
| Starch, U.S.P. | 350 |
| Talc, U.S.P. | 250 |
| Calcium stearate | 35 |

The powdered bis(5-mercaptopyridoxine) ethane-1,2-disulfonate is granulated with a 4% w./v. aqueous solution of methylcellulose U.S.P. (1500 cps.). To the dried granules is added a mixture of the remainder of the ingredients and the final mixture compressed into tablets of proper weight.

2. Capsules — 10,000 Two-piece hard gelatine capsules for oral use, each containing 250 mg. of bis(5-mercaptopyridoxine) ethane-1,2-disulfonate are prepared from the following ingredients:

|  | Gm. |
|---|---|
| bis(5-mercaptopyridoxine) ethane-1,2-disulfonate | 2500 |
| Lactose, U.S.P. | 1000 |
| Starch, U.S.P. | 300 |
| Talc, U.S.P. | 65 |
| Calcium stearate | 25 |

The powdered bis(5-mercaptopyridoxine) ethane-1,2-disulfonate is mixed with the starch-lactose mixture followed by the talc and calcium stearate. The final mixture is then encapsulated in the usual manner. Capsules containing 10, 25, 50, and 100 mg. of 5-mercaptopyridoxine ethane-1,2-disulfonate are also prepared by substituting 100, 250, 500, and 1000 gm. for 2500 gm. in the above formulation.

3. Soft Elastic Capsules — One-piece soft elastic capsules for oral use, each containing 500 mg. of bis(5-mercaptopyridoxine) ethane-1,2-disulfonate are prepared in the usual manner by first dispersing the powdered active material in sufficient corn oil to render the material capsulatable.

4. Aqueous Suspension — An aqueous suspension for oral use containing in each 5 ml., 1 gm. of bis(5-mercaptopyridoxine) ethane-1,2-disulfonate is prepared from the following ingredients:

| bis(5-mercaptopyridoxine) ethane-1,2-disulfonate | gm. | 2000 |
|---|---|---|
| Methylparaben, U.S.P. | gm. | 7.5 |
| Propylparaben, U.S.P. | gm. | 2.5 |
| Saccharin sodium | gm. | 12.5 |
| Glycerin | ml. | 3000 |
| Tragacanth powder | gm. | 10 |
| Orange oil flavor | gm. | 10 |
| F.D.&C. orange dye | gm. | 7.5 |

| -continued |
| --- |
| Deionized water, q.s. to 10 liters |

What is claimed is:

1. A compound of formula:

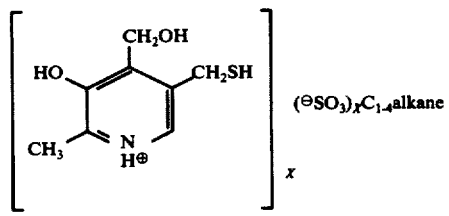

wherein X is 1 or 2, and $C_{1-4}$ alkane is straight or branched chain.

2. The compound of claim 1 which is bis(5-mercaptopyridoxine) ethane-1,2-disulfonate.

3. A method of treating rheumatoid arthritis which comprises the administration to a patient in need of such treatment an effective amount of a compound of formula:

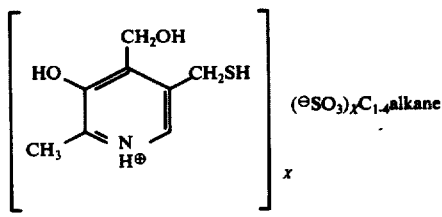

wherein X is 1 or 2, and $C_{1-4}$ alkane is straight or branched chain.

4. The method of treatment of claim 3 wherein the compound is bis(5-mercaptopyridoxine) ethane-1,2-disulfonate.

5. A pharmaceutical composition for treating rheumatoid arthritis comprising a carrier and an effective amount of a compound of formula:

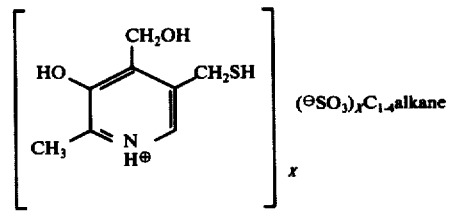

wherein X is 1 or 2, and $C_{1-4}$ alkane is straight or branched chain.

6. The pharmaceutical composition of claim 5 wherein the compound is bis(5-mercaptopyridoxine) ethane-1,2-disulfonate.

* * * * *